United States Patent
Knutsen et al.

(10) Patent No.: US 9,700,548 B2
(45) Date of Patent: Jul. 11, 2017

(54) ANTIHISTAMINES COMBINED WITH DIETARY SUPPLEMENTS FOR IMPROVED HEALTH

(75) Inventors: Lars Jacob Stray Knutsen, West Chester, PA (US); Judi Lois Knutsen, Cambridge (GB)

(73) Assignee: REQUIS PHARMACEUTICALS INC., West Chester, PA (US)

( * ) Notice: Subject to any disclaimer, the term of this patent is extended or adjusted under 35 U.S.C. 154(b) by 0 days.

(21) Appl. No.: 14/124,748

(22) PCT Filed: Jun. 8, 2012

(86) PCT No.: PCT/US2012/041655
§ 371 (c)(1),
(2), (4) Date: Mar. 5, 2014

(87) PCT Pub. No.: WO2012/170883
PCT Pub. Date: Dec. 13, 2012

(65) Prior Publication Data
US 2014/0199417 A1    Jul. 17, 2014

Related U.S. Application Data

(60) Provisional application No. 61/495,185, filed on Jun. 9, 2011.

(51) Int. Cl.
| | |
|---|---|
| A61K 31/4402 | (2006.01) |
| A61K 45/06 | (2006.01) |
| A61K 31/4415 | (2006.01) |
| A61K 31/56 | (2006.01) |
| A61K 31/495 | (2006.01) |
| A61K 31/4045 | (2006.01) |
| A23L 2/52 | (2006.01) |
| A61K 31/405 | (2006.01) |
| A61K 36/84 | (2006.01) |

(52) U.S. Cl.
CPC .......... *A61K 31/4415* (2013.01); *A23L 2/52* (2013.01); *A61K 31/405* (2013.01); *A61K 31/4045* (2013.01); *A61K 31/4402* (2013.01); *A61K 31/495* (2013.01); *A61K 31/56* (2013.01); *A61K 36/84* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 5,990,147 | A * | 11/1999 | Aslanian | C07D 233/64 514/400 |
| 2002/0004049 | A1 | 1/2002 | Hudson et al. | |
| 2002/0119196 | A1 * | 8/2002 | Parikh | A61K 9/0056 424/472 |
| 2004/0101563 | A1 * | 5/2004 | Kundu | A61K 9/0095 424/488 |
| 2004/0247646 | A1 | 12/2004 | Ivory et al. | |
| 2004/0247647 | A1 * | 12/2004 | Ivory | A23L 27/79 424/440 |
| 2005/0164987 | A1 | 7/2005 | Barberich | |
| 2007/0004671 | A1 * | 1/2007 | Agarwal et al. | 514/53 |
| 2007/0123571 | A1 | 5/2007 | Raj et al. | |
| 2010/0291204 | A1 | 11/2010 | Cuine et al. | |

FOREIGN PATENT DOCUMENTS

| | | |
|---|---|---|
| JP | 2004-137042 | 5/2004 |
| JP | 2005-320254 | 11/2005 |
| WO | PCT/US2004/043308 A2 | 7/2005 |
| WO | PCT/GB2004/002330 A1 | 12/2005 |
| WO | PCT/FR2006/001830 A1 | 2/2007 |

OTHER PUBLICATIONS

Sutton, D.A., Moldofsky, H. and Badley, E.M. Insomnia and Health Problems in Canadians, Sleep, 2001, 24, 665-670.
Fullerton D. The economic impact of insomnia in managed care: A clearer picture emerges. American Journal of Managed Care, 2006, 12, 246-252.
Roth,T. Insomnia: Definition, Prevalence, Etiology, and Consequences, Journal of Clinical Sleep Medicine, 2007, 3, (suppl.):S7-S10).
Cajochen, C.; Krauchi, K.; Wirz-Justice, A. Role of melatonin in the regulation of human circadian rhythms and sleep Journal of Neuroendocrinology, 2003, 15, 432-437.
Riemann, D.; Feige, B.; Hornyak, M.; Koch, S.; Hohagen, F.; Voderholzer, U. The tryptophan depletion test: impact on sleep in primary insomnia—a pilot study. Psychiatry Research, 2002, 109, 129-135.
Ruddick, J.P.; Evans, A.K.; Nutt, D.J.; Lightman, S.L., Rook, G.A., Lowry, C.A. Tryptophan metabolism in the central nervous system: medical implications. Expert Rev. Mol. Medicine, 2006, 8, 1-27.
Price, J.M. Vitamin B6 and tryptophan metabolism in man. Edited by Yamada, K. Symp. Pyridoxal Enzymes, 3rd., 1968, 213.
Hamon, M.; Bourgoin, S.; Artaud, F.; Hery, F. Rat brain stem tryptophan hydroxylase: mechanism of activation by calcium. J. Neurochem. 1977, 28, 811-418.
Lysz, T.W.; Sze, P.Y. Activation of brain tryptophan hydroxylase by a phosphorylating system. J. Neurosci. Res., 1978, 3, 411-418.

(Continued)

*Primary Examiner* — James H Alstrum Acevedo
*Assistant Examiner* — Roy Teller
(74) *Attorney, Agent, or Firm* — Merchant & Gould P.C.

(57) ABSTRACT

The present invention provides combinations comprising a sedating antihistamine and selected indole-based natural products such as L-tryptophan, 5-hydroxytryptophan and melatonin, along with pharmaceutically acceptable calcium and magnesium salts and selected B vitamins. These combinations are useful in providing a medicament for improving sleep in mammals, especially humans.

7 Claims, 1 Drawing Sheet

(56) References Cited

OTHER PUBLICATIONS

Boadle-Biber, M.C. Effect of calcium on tryptophan hydroxylase from rat hind brain, Biochemical Pharmacology, 1975, 24, 1455-1460.
Prospero-Garcia, O.; Criado J.R. and Henricksen, S.J., A method for investigating sleep Pharmacology of Ethanol and Glutamate Antagonists on Rodent Sleep: A Comparative Study. Pharmacology Biochemistry and Behavior, 1994, 49, 413-416.
Weeks, Formulations of dietary supplements and herbal extracts for relaxation and anxiolytic action; Relarian(tm); Med Sci Monit, 2009, vol. 15(11) RA256=262.

\* cited by examiner

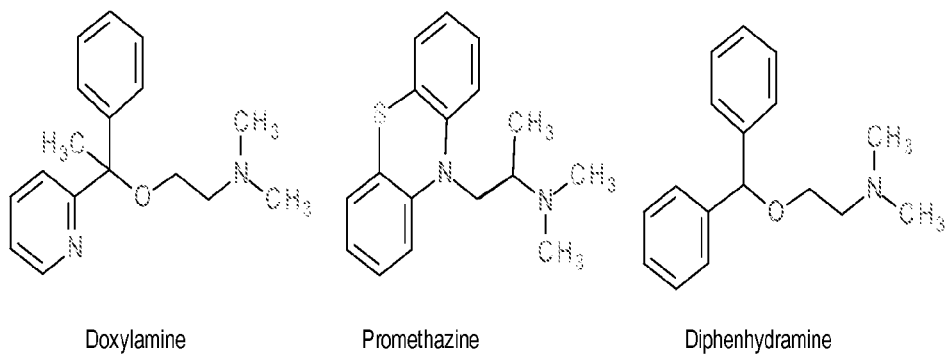
Figure 1: Examples of preferred antihistamine drugs
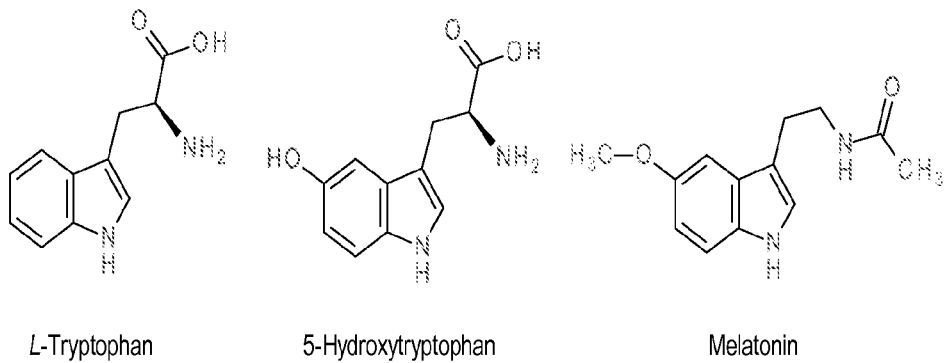
Figure 2: Representative indole-based dietary supplements

ANTIHISTAMINES COMBINED WITH DIETARY SUPPLEMENTS FOR IMPROVED HEALTH

CROSS REFERENCE TO RELATED APPLICATIONS

This application is the US national application of PCT/US2012/041655, filed on Jun. 8, 2012 and which claims priority to U.S. Provisional Application No. 61/495,185 filed on Jun. 9, 2011, the disclosure of which is herein incorporated by reference in its entirety.

FIELD OF THE INVENTION

The present invention is directed to novel combinations of sedating antihistamines and certain indole-based dietary supplements, and to their use for improving the health of human subjects, including improving sleep, inducing restorative sleep function, the treatment of insomnia and other sleep-related problems such as issues with circadian rhythm, shift work disorder and jet lag.

BACKGROUND OF INVENTION

Antihistamine drugs, i.e. antagonists or inverse agonists of the histamine $H_1$ receptor have been known since the 1940's and 1950's and have been utilized with success as anti-allergy agents. These drugs have proved to be generally safe in low dose and normal use. One of the observed side-effects of these antihistamines has been sedation and therefore a range of clinically well-proven antihistamine-based drugs are now available in many territories as over-the-counter (OTC) sleep-aids, which are distinguished from prescription sleep drugs by their milder effect, and their availability in most pharmaceutical markets without a prescription.

Antihistamines which are established for use as anti-allergy agents and have a range of sedative effects and therefore have potential use as sleep-aids include Cetirizine, Chlorpheniramine, Clemastine, Desloratadine, Dexchlorpheniramine, Dimenhydrinate, Dimetindene, Diphenhydramine, Doxylamine, Ebastine, Embramine, Fexofenadine, Levocetirizine, Loratadine, Meclozine, Olopatadine, Pheniramine, Promethazine and Triprolidine.

According to the fourth edition of the Diagnostic and Statistical Manual of Mental Disorders (DSM-IV-TR), insomnia is characterized by one or more of these sleep complaints, which cause clinically significant impairment of daytime functioning:

Difficulty initiating sleep
Difficulty maintaining sleep
Nonrestorative sleep

One of the functions of sleep is the maintenance, restoration, and repair of the body. Sleep is generally characterized by anabolic activity (including building and remodeling) in muscle, bone, connective tissue, skin, and major organs including the brain. One result of this activity is restoration of function including physical and mental performance such as stamina, energy, and mental alertness. Lack of sleep has consequences for daytime performance and when chronic, for mental health.

Insomnia has been shown to be highly prevalent among the non-institutionalized Canadian population age 15 and older. The disorder is associated with a very stressful life, severe pain and dissatisfaction with one's health, these factors demonstrated the highest association with insomnia (Sutton, D. A., Moldofsky, H. and Badley, E. M. Insomnia and Health Problems in Canadians, *Sleep,* 2001, 24, 665-670). Around 24% of the total Canadian population age 15 and older reported experiencing insomnia. As expected the prevalence of insomnia increased with age, from one fifth of those age 15 to 24 years to slightly more than one third among those 75 years and older. The presence of circulatory, digestive and respiratory disease, allergy, migraine, and rheumatic disorders show the highest associations with insomnia together with pain, life stress, and health dissatisfaction. These findings emphasize the importance of recognizing and addressing chronic physical health conditions, pain, and life stress issues in the diagnosis and treatment of insomnia.

It is estimated that insomnia is responsible for over $14 billion in direct healthcare costs each year in the United States, and untold billions in lost productivity. Overall, it is believed that the direct and indirect costs attributable to insomnia exceed $100 billion per year in the USA alone (Fullerton D. The economic impact of insomnia in managed care: A clearer picture emerges. *American Journal of Managed Care,* 2006, 12, 246-252). In its initial stages, insomnia occurs when predisposing factors, such as illness or pain, combine with precipitating or triggering factors, typically life stress and anxiety, to bring about issues with falling asleep, mid-nocturnal or early morning awakening or poor sleep quality. Once insomnia begins, perpetuating factors, including a range of largely ineffective compensatory behaviors (e.g. daytime naps, sleeping in on weekends) and negative thoughts can create a vicious cycle, transforming an acute problem into a more chronic one. Without intervention, ineffective coping strategies can distort the individual's sleep-wake cycle, while the negative thoughts about sleep trigger anxiety and create a self-fulfilling prophecy. If people believe they will not fall asleep, then it is likely they will be tense at bedtime, and as a result can find it difficult to sleep, and pharmacological intervention will be required. Some patients may be even embarrassed to visit their physician for such an issue or may have had bad experiences with early prescription sleep medicines. Therefore a significant market in non-prescription sleep aids has developed, especially in North America. However, there is a constant need for novel and improved products as existing products have their problems.

Insomnia is associated with a number of health issues. In a 2007 review article (Roth, T. Insomnia: Definition, Prevalence, Etiology, and Consequences, *Journal of Clinical Sleep Medicine,* 2007, 3, (suppl.):S7-S10). It is concluded that chronic insomnia is highly prevalent and affects approximately 30% of the general US population. Insomnia impairs cognitive and physical functioning and is associated with a wide range of impaired daytime functions across a number of emotional, social, and physical domains. Compared with good sleepers, people with persistent sleep disturbances are more prone to accidents, have higher rates of work absenteeism, diminished job performance, decreased quality of life, and increased health care utilization. Various risk factors associated with increased prevalence of chronic insomnia include older age, female gender, and co-morbid medical and psychiatric conditions. Approximately 40% of adults with insomnia also have a diagnosable psychiatric disorder—most notably depression. A co-morbid psychiatric disorder such as depression or anxiety may be a consequence of—as well as a risk factor for—disrupted sleep.

Therefore an inability to sleep is often a symptom of stress, and if untreated can lead to severe anxiety and depression. A lot of patients self-medicate when suffering from mild and temporary insomnia, and one of the most-used OTC or general sale treatments is with antihistamines. The subject matter of this invention is that the effect of these sleep-aids be improved further with addition of indole-based dietary supplements including L-tryptophan, 5-hydroxytryptophan (5-HTP) and melatonin to the antihistamine drug formulation.

Doxylamine is a preferred member of the ethanolamine class of antihistamine drugs since it possesses an anti-allergy effect in human subjects superior to almost every other antihistamine on the market, with the possible exception of diphenhydramine. It is also the most effective sedative available in general sale the United States, and is seen as more sedating than some prescription hypnotics. One study reputedly found that doxylamine succinate was more effective than the barbiturate phenobarbital for use as a sedative (http://www.drugbank.ca/drugs/DB00366).

PCT Int. Appl. WO 2005/063297 relates to pharmaceutical compositions, in particular controlled-release oral dosage forms, comprising a sedative agent, and melatonin or a melatonin analog. In a preferred embodiment, the sedative agent is eszopiclone.

JP 2005320254 claims certain combinations of antihistamines, for example diphenhydramine and melatonin as hypnotics.

PCT Int. Appl. WO 2005/123074 discloses a method is disclosed for the treatment of sleep disorders. The method involves administration of triprolidine, in combination with at least one further active pharmaceutical agent, for enabling an individual to wake refreshed after sleep and the method of treating such an individual with triprolidine. Use of triprolidine, in combination with at least one further active pharmaceutical agent, as active ingredient in the manufacture of a composition for the treatment of sleep disorders is also described.

PCT Int. Appl. WO 2007/020337 relates to the combination of: a short-acting hypnotic agent which is selected from among a modulator of receptors GABA-A, a benzodiazepine, a phenothiazine, a melatonin derivative and a melatonin receptor agonist; and a long-acting hypnotic agent which is selected from among a modulator of receptors GABA-A, a benzodiazepine, an antagonist of receptors $5HT_{2A}$ and a calcium ion modulator, for the treatment of sleep disorders.

U.S. Pat. Appl. Publ. US 20020004049 describes compositions comprising partially defatted meal from a plant source containing protein-bound tryptophan, preferably squash seeds, and, optionally, a carbohydrate source provided in an amount capable of facilitating transport of in vivo generated tryptophan across the blood brain barrier. Also described are dietary supplements, foods and beverages comprising the composition of the invention to induce sleep.

In a similar manner to many other first-generation antihistamines, diphenhydramine causes strong histamine $H_1$ receptor antagonist-mediated sedation. Diphenhydramine has also been utilized as an anxiolytic agent because of this effect. However, given its pharmacology, diphenhydramine also has anticholinergic properties, leading to the potential side-effects of dry mouth and throat, increased heart rate, pupil dilation, urinary retention, constipation, and, at high doses, hallucinations or delirium. Further side-effects include motor impairment (ataxia), flushed skin, blurred vision at nearpoint owing to lack of accommodation (cycloplegia), abnormal sensitivity to bright light (photophobia), difficulty concentrating, short-term memory loss, visual disturbances, irregular breathing, dizziness, irritability, itchy skin, confusion, decreased body temperature (in general, in the hands and/or feet), erectile dysfunction, and excitability. (see http://www.drugs.com/sfx/diphenhydramine-side-effects.html).

In the 1960', the antihistamine diphenhydramine was found to inhibit reuptake of the important neurotransmitter serotonin, also known as 5-hydroxytryptamine (5-HT). This discovery led to a search for viable antidepressants with similar structures and lowered side-effects, culminating in the invention of fluoxetine (Prozac), a selective serotonin reuptake inhibitor (SSRI). A similar SAR study had previously led to the synthesis of the first SSRI, zimelidine, from brompheniramine, also an antihistamine. This observation indicates that some antihistamines, including doxylamine, may have a more specific mechanism of action compared to earlier drugs.

Furthermore, the antihistamine promethazine has a strong sedative effect and in some countries is prescribed for insomnia when benzodiazepines are contraindicated. It is available OTC in the United Kingdom, Australia, Switzerland, and many other countries, but by prescription only in the United States.

SUMMARY OF THE INVENTION

The present invention is directed to novel combinations of sedating antihistamines and at least one, and preferably two or more dietary supplements, which can be indole-based, such as tryptophan, 5-hydroxytryptophan, serotonin, N-acetyl-5-hydroxytryptamine and melatonin, and to their use for improving the health of human subjects, including the treatment of insomnia and other sleep-related problems such as problems with circadian rhythm, shift work disorder and jet lag.

Dietary Supplements: this invention is directed in part to the use of indole-based dietary supplements in combination with antihistamines to provide an enhanced effect in the treatment of temporary or chronic insomnia. Examples of dietary supplements with utility in such combinations are L-tryptophan, 5-hydroxytryptophan, serotonin, N-acetyl-5-hydroxytryptamine and melatonin.

Melatonin has a number of beneficial effects, particularly in the regulation of sleep. Studies of melatonin have led to the idea that melatonin is an internal sleep "facilitator" in humans, and therefore useful in the treatment of insomnia and the readjustment of circadian rhythms. There is evidence that administration of melatonin is able: (i) to induce sleep when the homeostatic drive to sleep is insufficient; (ii) to inhibit the drive for wakefulness emanating from the circadian pacemaker; and (iii) induce phase shifts in the circadian clock such that the circadian phase of increased sleep propensity occurs at a new, desired time. Therefore, exogenous melatonin can act as soporific agent, a chronohypnotic, and/or a chronobiotic, and role of melatonin in the regulation of sleep, and the use of exogenous melatonin to treat sleep or circadian rhythm disorders is described (Cajochen, C.; Krauchi, K.; Wirz-Justice, A. Role of melatonin in the regulation of human circadian rhythms and sleep. *Journal of Neuroendocrinology*, 2003, 15, 432-437). The use of melatonin in combination with antihistamines will therefore provide an improved sleep-aid, especially in the treatment of circadian rhythm sleep disorders resulting in insomnia and poor sleep quality.

Melatonin has other documented health benefits, having been studied in the treatment of cancer, immune disorders, cardiovascular diseases, depression, seasonal affective disorder (SAD), and sexual dysfunction. It has potent antioxidant properties.

L-Tryptophan is an essential amino acid, meaning that it cannot be synthesized by the human body and therefore must be part of our diet. Amino acids, including tryptophan, act as building blocks in protein biosynthesis and in addition, tryptophan functions as a biochemical precursor for serotonin, and in turn, melatonin Serotonin has been implicated in the regulation of sleep, depression, anxiety, appetite, sexual behavior, and body temperature.

Serotonin is produced by biosynthesis in 2 steps from tryptophan via the enzymes tryptophan hydroxylase and aromatic amino acid decarboxylase. Serotonin, in turn, can be converted to the neurohormone melatonin, via the action of N-acetyltransferase and 5-hydroxyindole-O-methyltransferase. Niacin is synthesized from tryptophan via kynurenine and quinolinic acids as key biosynthetic intermediates.

In recent years, research has illustrated the utility of L-tryptophan's to treat insomnia. One study found that tryptophan depletion contributed to insomnia; 15 subjects suffering from insomnia were dosed with an amino acid drink that depleted tryptophan, and the participants' sleep patterns were studied. It was found that that sleep was significantly disrupted after tryptophan levels were lowered (Riemann, D.; Feige, B.; Hornyak, M.; Koch, S.; Hohagen, F.; Voderholzer, U. The tryptophan depletion test: impact on sleep in primary insomnia—a pilot study. Psychiatry Research, 2002, 109, 129-135).

5-Hydroxytryptophan (5-HTP) is a metabolite of tryptophan. In a further embodiment of this invention the indole-based dietary supplement is 5-hydroxytryptophan and in combination with antihistamines finds utility in the treatment of disturbed sleep, insomnia and other sleep-related problems such as issues with circadian rhythm, shift work disorder and jet lag.

An alternative pathway of tryptophan metabolism takes place in a series of steps initially involving the enzyme indolamine-2,3-dioxygenase, proceeding via kynurenine derivatives and ultimately leads to Niacin (vitamin $B_3$) (Ruddick, J. P.; Evans, A. K.; Nutt, D. J.; Lightman, S. L., Rook, G. A., Lowry, C. A. Tryptophan metabolism in the central nervous system: medical implications. *Expert Rev. Mol. Medicine,* 2006, 8, 1-27). Co-dosing with Niacin as part of this novel combination therefore will direct tryptophan metabolism in the direction of 5-HT and its immediate precursor 5-hydroxytryptamine (5-HTP).

Pyridoxine, a $B_6$ vitamin, is involved for the production of 5-HT, as the precursor to pyridoxal phosphate, a cofactor for the enzyme aromatic amino acid decarboxylase, which is responsible for converting 5-HTP into serotonin. When humans are fed diets low in pyridoxine, abnormal metabolism of tryptophan occurs within 5-15 days (Price, J. M. Vitamin $B_6$ and tryptophan metabolism in man. Edited by Yamada, K. Symp. Pyridoxal Enzymes, 3rd., 1968, 213).

Therefore in a further embodiment of this invention, the presence of vitamins such as $B_3$ and $B_6$ that support L-tryptophan metabolism in the direction of 5-HT may be included the novel combination to provide a more effective formulation for sleep improvement in mammals.

The activity of soluble tryptophan hydroxylase from rat brain stem was increased in presence of mM concentrations of calcium, and in addition, the optimal pH for the enzymic activity was shifted from 7.6 to 7.9 following activation by calcium, sodium dodecyl sulphate or trypsin. Under the assay conditions used for measuring tryptophan hydroxylase activity, calcium also stimulated a neutral proteinase. Hamon, M.; Bourgoin, S.; Artaud, F.; Hery, F. Rat brain stem tryptophan hydroxylase: mechanism of activation by calcium. *J. Neurochem.* 1977, 28, 811-418.

Tryptophan 5-hydroxylase (TPH) is the rate-limiting enzyme in the conversion of tryptophan to 5-HT. A significant activation of tryptophan hydroxylase (TPH) was achieved by the addition of 1 mM ATP and 10 mM $MgCl_2$ to supernatant prepared from mouse midbrain. The activation produced an increase of enzyme activity by 50-70% above control. The enzyme activation by $Mg^{2+}$-ATP was totally retained after dialysis, thus excluding the possibility of an allosteric effect. In contrast to the activation (Lysz, T. W.; Sze, P. Y. Activation of brain tryptophan hydroxylase by a phosphorylating system. *J. Neurosci. Res.,* 1978, 3, 411-418).

In a further embodiment of this invention, minerals such as calcium and magnesium support L-tryptophan metabolism in the direction of 5-HT may be included the novel combination to provide a more effective formulation for sleep improvement in mammals.

In a further embodiment of this invention, compositions of antihistamines and indole-based dietary supplements are claimed which have utility in the treatment of jet lag, also known as jet lag disorder. This disorder is a temporary sleep disorder that affects people who quickly travel across multiple time zones. Jet lag is caused by a disruption to the body's internal clock or circadian rhythms which tell the body when to be awake and when to sleep. The more time zones crossed, the more severe the experience of jet lag will tend to be. Jet lag can cause daytime fatigue, a feeling of unease or anxiety, difficulty staying alert as well as gastrointestinal problems. Jet lag disorder is temporary, but it can significantly degrade the experience of travel and certainly the insomnia combined with issues of circadian rhythm and concentration can result in poor decision making, which is especially relevant for business travelers.

In a further embodiment of this invention, compositions of antihistamines and indole-based dietary supplements are claimed which have utility in the treatment of sleep issues in the elderly.

In a further embodiment of this invention, compositions of these indole-based dietary supplements combined with antihistamines can improve sleep and symptoms of Mild Cognitive Impairment in elderly patients.

BRIEF DESCRIPTION OF THE DRAWINGS

FIG. 1 shows examples of preferred antihistamine drugs used in the present invention.

FIG. 2 shows examples of indole-based dietary supplements.

DETAILED DESCRIPTION OF THE INVENTION

The present invention is directed to novel combinations of sedating antihistamines and certain indole-based dietary supplements, and to their use for improving the health of human subjects, including the treatment of insomnia and other sleep-related problems such as issues with circadian rhythm and jet lag. A further embodiment of the invention is for specific combinations of a pharmacologically active and bioavailable antihistamine ($H_1$ receptor antagonist), a melatonin component and a tryptophan component. A further embodiment of the invention is for specific combinations of a pharmacologically active and bioavailable antihistamine (H1 receptor antagonist), a melatonin component and a tryptophan component, optionally combined with one or more vitamins such as $B_3$ and $B_6$, and one or more minerals such as calcium and magnesium. These compositions, and methods of use thereof, are useful for to provide a more effective formulation for sleep improvement in mammals more directly inducing the benefits of restorative sleep.

Various documents including, for example, publications and patents, are recited throughout this disclosure. All such documents are hereby incorporated by reference. Trade names for products or components including various ingredients may be referenced herein. The inventors herein do not intend to be limited by materials under a certain trade name.

In the description of the invention various embodiments or individual features are disclosed. As will be apparent to the ordinarily skilled practitioner, all combinations of such embodiments and features are possible and can result in preferred executions of the present invention. The compositions herein may comprise, consist essentially of, or consist of any of the elements as described herein.

While various embodiments and individual features of the present invention have been illustrated and described, various other changes and modifications can be made without departing from the spirit and scope of the invention. As will also be apparent, all combinations of the embodiments and features taught in the foregoing disclosure are possible and can result in preferred executions of the invention.

With respect to dosing preferences, dosage levels are developed based on typical human subjects (e.g. a 70 kg subject). If the present composition is used in other mammals or in various human subjects, it may be necessary to modify the dosage. Modification of dosages based on the needs of the subject is well within the skill of the ordinary artisan. It is therefore understood that these dosage ranges are by way of example only, and that daily administration can be adjusted depending on various factors. The specific dosage of the compound to be administered, and the duration of treatment are interdependent. The dosage and treatment regimen will also depend upon such factors as the specific compound used, the treatment indication, the efficacy of the compound, the personal attributes of the subject (such as, for example, weight, age, gender, and medical condition of the subject), and compliance with the treatment regimen.

In a further embodiment of this invention, novel compositions of antihistamines, indole-based dietary supplements such as tryptophan, 5-hydroxytryptophan and melatonin in combination with niacin (also known as vitamin $B_3$, nicotinic acid or vitamin PP) are claimed for the treatment of insomnia and other sleep-related problems such as issues with circadian rhythm and jet lag. Co-dosing of vitamins, for example niacin, assists in the metabolism of tryptophan to serotonin in human subjects.

In a further embodiment of this invention, novel compositions of antihistamines, indole-based dietary supplements such as tryptophan, 5-hydroxytryptophan and melatonin in combination with vitamin $B_6$ are claimed for the treatment of insomnia and other sleep-related problems such as issues with circadian rhythm and jet lag. Co-dosing of vitamins, for example $B_6$, assists in the metabolism of tryptophan to serotonin in human subjects.

In a further embodiment of this invention, novel compositions of antihistamines, indole-based dietary supplements such as tryptophan, 5-hydroxytryptophan and melatonin in combination with pharmaceutically acceptable calcium salts are claimed for the treatment of insomnia and other sleep-related problems such as issues with circadian rhythm and jet lag. Representative pharmaceutically acceptable calcium salts are calcium hydrochloride, calcium tartrate, calcium maleate, calcium citrate, calcium phosphate, calcium acetate, calcium lactate calcium fumarate, calcium sulfate, calcium bromide, calcium mesylate, calcium palmoate, calcium iodide, calcium nitrate and calcium methylsulfate.

These novel combinations of sedating antihistamines and indole-based dietary supplements with calcium salts have utility in the treatment of insomnia and other sleep-related problems such as issues with circadian rhythm, shift work disorder and jet lag. It is known that calcium stimulates the metabolism of tryptophan and the presence of calcium salts will bring about more rapid formation of serotonin (Boadle-Biber, M. C. Effect of calcium on tryptophan hydroxylase from rat hind brain, *Biochemical Pharmacology,* 1975, 24, 1455-1460).

In a further embodiment of this invention, compositions of antihistamines and indole-based dietary supplements with optional addition of niacin and calcium salts are provided in a liquid form as a drink to be taken at bedtime to improve sleep. In a preferred embodiment the liquid formulation can be ingested either before or during or after a long aircraft flight to aid rest and sleep as well as treating the symptoms of jet lag including issues with circadian rhythm. The presence of vitamins, sugars, sources of complex carbohydrates and other ingredients and formulations are also added, familiar to those skilled in the art of preparing beverages.

Methods of Use

The methods of the present invention comprise orally administering (i.e., through ingestion) a composition of the present invention to a mammal, preferably a human, to provide various health benefits, including treatment of insomnia and inducing restorative sleep function and combinations thereof. The compositions of the present invention are most preferably ingested by consumers primarily desiring restorative sleep function while taking advantage of the restorative actions of the mammalian body during rest sleep. The compositions of this invention may also be ingested as a supplement to normal dietetic requirements. Frequency of administration is not limited. However, such administration for treatment of insomnia is typically at least once weekly, more preferably at least 3 times weekly, and most preferably at least once daily around bedtime.

As used herein, "restorative sleep function" refers to alleviation of any circadian rhythm phase-shifting effect, jet lag, winter depression, shift work-related desynchronies, sleep phase disorders, and other sleep disorders, improvement in sleep quality, improvement of sleep duration, and combinations thereof.

As used herein, the term "orally administering" with respect to the mammal (preferably, human) means that the mammal ingests or is directed to ingest (preferably, for the purpose of providing one or more of the health benefits described herein) one or more compositions of the present invention. In one embodiment, the composition is formulated as a tablet, capsule, food or beverage composition. Wherein the mammal is directed to ingest one or more of the compositions, such direction may be that which instructs and/or informs the user that use of the composition may and/or will provide one or more general health and/or general physiological benefits including, but not limited to, restorative sleep function.

The following are non-limiting examples of Methods which can be utilized to provide tablet formulations of the novel combinations which are useful in providing a medicament for improving sleep in mammals, especially humans.

Method A

A tablet formulation is prepared for use in treating sleep disorders in mammals comprising 0.001 g to 0.05 g of a suitable sedating antihistamine, for example doxylamine as its pharmaceutically acceptable salt, for example its succinate salt form, 0.0001 g to 0.01 g of melatonin, 0.001 g to 1.0 g of L-tryptophan, 0.01 g to 0.05 g of niacin, 0.001 g to 0.01 g of pyridoxine, 0.01 to 1.0 g of a suitable mineral salt of calcium, for example calcium citrate and 0.005 to 0.5 g of a magnesium compound such as magnesium oxide. Suitable excipients for this tablet formulation include dicalcium phosphate, acceptable dyes such as FD&C Blue #1 aluminum lake, magnesium stearate, microcrystalline cellulose and sodium starch glycolate. The tablet is dosed to human subjects in order to improving their health, especially in the treatment of sleep problems, including inducing restorative sleep function, in the treatment of insomnia and other sleep-related problems such as issues with circadian rhythm, shift work disorder and jet lag.

Method B

A tablet formulation is prepared for use in treating sleep disorders in mammals comprising 0.001 g to 0.05 g of a suitable sedating antihistamine, for example doxylamine as its pharmaceutically acceptable salt, for example its succinate salt form, 0.0001 g to 0.01 g of melatonin, 0.001 g to 1.0 g of L-tryptophan, 0.01 g to 0.05 g of niacin and 0.001 g to 0.01 g of pyridoxine. Suitable excipients for this tablet formulation include dicalcium phosphate, calcium citrate, acceptable dyes such as FD&C Blue #1 aluminum lake, magnesium stearate, microcrystalline cellulose and sodium starch glycolate. The tablet is dosed to human subjects in order to improving their health, especially in the treatment of sleep problems, including inducing restorative sleep function, in the treatment of insomnia and other sleep-related problems such as issues with circadian rhythm, shift work disorder and jet lag.

Method C

A tablet formulation is prepared for use in treating sleep disorders in mammals comprising 0.001 g to 0.05 g of a suitable sedating antihistamine, for example doxylamine as its pharmaceutically acceptable salt, for example its succinate salt form, 0.0001 g to 0.01 g of melatonin, 0.001 g to 1.0 g of L-tryptophan, 0.01 g to 0.05 g of niacin and 0.01 g to 0.1 g of theanine. Suitable excipients for this tablet formulation include dicalcium phosphate, calcium citrate, acceptable dyes such as FD&C Blue #1 aluminum lake, magnesium stearate, microcrystalline cellulose and sodium starch glycolate. The tablet is dosed to human subjects in order to improving their health, especially in the treatment of sleep problems, including inducing restorative sleep function, in the treatment of insomnia and other sleep-related problems such as issues with circadian rhythm, shift work disorder and jet lag.

Method D

A tablet formulation is prepared for use in treating sleep disorders in mammals comprising 0.005 g to 0.01 g of a suitable sedating antihistamine, for example diphenhydramine as its pharmaceutically acceptable salt, for example its hydrochloride or citrate salt form, 0.0001 g to 0.01 g of melatonin, 0.001 g to 1.0 g of L-tryptophan, 0.01 g to 0.05 g of niacin, 0.001 g to 0.01 g of pyridoxine, 0.01 to 1.0 g of a suitable mineral salt of calcium, for example calcium citrate and 0.005 to 0.5 g of a magnesium compound such as magnesium oxide. Suitable excipients for this tablet formulation include dicalcium phosphate, acceptable dyes such as FD&C Blue #1 aluminum lake, magnesium stearate, microcrystalline cellulose and sodium starch glycolate. The tablet is dosed to human subjects in order to improving their health, especially in the treatment of sleep problems, including inducing restorative sleep function, in the treatment of insomnia and other sleep-related problems such as issues with circadian rhythm, shift work disorder and jet lag.

Method E

A tablet formulation is prepared for use in treating sleep disorders in mammals comprising 0.05 g to 0.1 g of a suitable sedating antihistamine, for example promethazine as its pharmaceutically acceptable salt, for example its hydrochloride salt form, 0.0001 g to 0.01 g of melatonin, 0.001 g to 1.0 g of L-tryptophan, 0.01 g to 0.05 g of niacin, 0.001 g to 0.01 g of pyridoxine, 0.01 to 1.0 g of a suitable mineral salt of calcium, for example calcium citrate and 0.005 to 0.5 g of a magnesium compound such as magnesium oxide. Suitable excipients for this tablet formulation include dicalcium phosphate, acceptable dyes such as FD&C Blue #1 aluminum lake, magnesium stearate, microcrystalline cellulose and sodium starch glycolate. The tablet is dosed to human subjects in order to improving their health, especially in the treatment of sleep problems, including inducing restorative sleep function, in the treatment of insomnia and other sleep-related problems such as issues with circadian rhythm, shift work disorder and jet lag.

Method F

A composition of 0.025 g doxylamine succinate, and the indole-based dietary supplements L-tryptophan (0.5 g) melatonin (0.005 g) were dissolved in pasteurized milk (250 mL) or a suitable fruit juice such as mango juice (250 mL), or a combination of juices. Niacin (0.25 g), vitamin $B_6$ (0.1 g) and calcium citrate (2.5 g) were added, followed by a source of carbohydrate, with vitamin C (0.5 g) and a suitable approved flavoring. This formulation is in a beverage form as a drink to be taken at bedtime to improve sleep, or before, during or after a long aircraft flight to aid rest and sleep as well as treating the symptoms of jet lag including disorders of circadian rhythm.

The following are non-limiting examples of the present compositions which are prepared utilizing conventional methods. The following examples are provided to illustrate the invention and are not intended to limit the scope thereof in any manner.

Example 1

Doxylamine succinate (0.80 g), L-tryptophan (32.50 g), melatonin (0.15 g), niacin (0.50 g) and pyridoxine (0.05 g) were all weighed on a Ohaus Explorer scale and combined with microcrystalline cellulose NF105 (Avicel™) (1.0 g). The ingredients were mixed thoroughly in a sterilized plastic container and the mixture was now ready for the capsule preparation procedure.

Utilizing a Jaansun® Capsule Machine 100, the mixture was carefully placed into #0 Clear Locking gelatin capsules (part #30-1988-5000EA, obtained from PCCA USA, 9901 S. Wilcrest Drive, Houston, Tex. 77099-5132) as described below, following the manufacturer's instructions closely.

The loader filled with empty capsules was placed on top of the separator plate so that it could slide freely from left to right. The loader was positioned on the blue rails and slid to the left or right till it stopped against one set of the blue posts. The white plate was then gently pushed into the spring block, and the capsules were allowed to drop through the loader plates with the lid end up. The loader was lifted up and off the capsule machine.

One of the retainer knobs was grasped and the separator plate was shaken to drop the capsules into the machine, ensuring that the capsules were sitting in the capsule machine so that the capsule tops could not rise above the blue metal ledge located just beneath the retainer knobs. Once the capsules had dropped into the machine, the capsules were gently tapped to ensure they were all at the required height; the procedure was then repeated for the remaining 50 capsules.

The loader was lifted up and off of the capsule machine, and all capsules were tapped gently to ensure they were sitting level in the capsule machine. The retainer plate was then placed on top of the separator plate with the beveled edges facing up, parallel to each set of retaining knobs. Each retainer knob was turned so that approximately ⅓ of the knob was covering the plate, and both pinch knobs were hand-tightened at the same time. The separator plate was then lifted up and off of the machine, and checked for capsule bases. Before setting the separator plate aside, it was ensured that the black retaining knobs were facing upwards.

The black pinch knobs were loosened and the capsules were allowed to drop down into the capsule machine so they were sitting flush with the top of the white pinch plate. The black pinch knobs were lightly tightened to hold the capsule bases in place during the filling process; the optional powder dam was placed on the top of the machine and the requisite clips applied over the powder dam and the short notch under the machine.

The thoroughly-mixed ingredients, as described above, were placed in powder form in the center of the machine and spread evenly over the top of the white pinch plate with a powder scraper. The machine was gently tapped in order to move the powders back and forth on the white pinch plate. The powders were tamped with a tamper to push air out of, and powder into the capsules, then the powder was redistributed over the capsules with a scraper as needed, checking for fill uniformity. This tapping, tamping, and scraping process was repeated until all the powder was neatly packed into the capsules.

Once it appeared that the majority of the powder has been packed into the capsules, the clips and powder dam were removed, and the tamper was used to check for capsule fill uniformity. If one end of tamper was sitting higher than the other end, the powder distribution was evened out using the tamper prongs as a scoop. The capsules were now ready to be reassembled by the following procedure.

The separator plate was placed on the machine with the notches to the front door, and both pinch knobs were loosened, but with the retainer knobs holding the retainer plate in place. The depth plate was gently bounced while gradually applying pressure to raise the depth plate up. Pressure was applied to both the front and back of the plates to bring all the capsules back together.

The separator plate was then lifted up, and checked underneath to ensure that all capsule bases had been reattached to the lids; and the retainer knobs were checked again to ensure that they are still holding the retainer plate in place. The separator plate was turned over and each capsule locked by gently pressing down on each one individually. The retainer plate was removed by rotating the retainer knobs and lifting the plate up and off the separator plate. The capsules were removed from the separator plate by turning the plate over and guiding the capsules into a towel, and then the four corners of the towel were brought together and the capsules were shaken, thereby cleaning the capsules and loading the capsule lids.

The batch of 100 capsules was then available for clinical evaluation, in a typical daily dose of 2 capsules at bedtime in subjects suffering from sleep problems, especially subjects who take dietary supplements ensuring healthy and adequate levels of the minerals calcium and magnesium.

Example 2

Doxylamine succinate (0.80 g), L-tryptophan (32.50 g), melatonin (0.15 g), niacin (0.50 g), pyridoxine (0.05 g), calcium citrate (0.25 g) and magnesium oxide (0.10 g) were all weighed carefully and combined with microcrystalline cellulose NF105 (Avicel™) (1.0 g). The ingredients were mixed thoroughly in a sterilized plastic container and the mixture was converted into a capsule formulation, as described in Example 1, but utilizing #0 Clear Locking gelatin capsules. The batch of 100 capsules was then available for clinical evaluation, in a typical daily dose of 2 capsules at bedtime in subjects suffering from sleep problems.

Example 3

Doxylamine succinate (0.80 g), L-tryptophan (32.50 g), melatonin (0.15 g) and niacin (0.50 g) were all weighed carefully and combined with microcrystalline cellulose NF105 (Avicel™) (1.0 g). The ingredients were mixed thoroughly in a sterilized plastic container and the mixture was converted into a capsule formulation, as described in Example 1. The batch of 100 capsules was then available for clinical evaluation, in a typical daily dose of 2 capsules at bedtime in subjects suffering from sleep problems, especially subjects who take dietary supplements ensuring healthy and adequate levels of the minerals calcium and magnesium.

Example 4

Doxylamine succinate (0.80 g), L-tryptophan (32.50 g), melatonin (0.15 g), niacin (0.50 g), powdered calcium citrate (0.25 g) and magnesium oxide (0.10 g) were all weighed carefully and combined with microcrystalline cellulose NF105 (Avicel™) (1.0 g). The ingredients were mixed thoroughly in a sterilized plastic container and the mixture was converted into a capsule formulation, as described in Example 1. The batch of 100 capsules was then available for clinical evaluation, in a typical daily dose of 2 capsules at bedtime in subjects suffering from sleep problems.

Example 5

Diphenhydramine hydrochloride (1.60 g), L-tryptophan (32.50 g), melatonin (0.15 g), niacin (0.50 g), pyridoxine (0.05 g), calcium citrate (0.25 g) and magnesium oxide (0.10 g) were all weighed carefully and combined with microcrystalline cellulose NF105 (Avicel™) (1.0 g). The ingredients were mixed thoroughly in a sterilized plastic container and the mixture was converted into a capsule formulation, as described in Example 1. The batch of 100 capsules was then available for clinical evaluation, in a typical daily dose of 2 capsules at bedtime in subjects suffering from sleep problems A method for assessing the effects of drugs on sleep time as well as differences in rapid eye-movement (REM) sleep, slow-wave sleep and wakefulness is illustrated in Example 5.

Example 6

Twenty-five male Sprague-Dawley rats (300-350 g at the time of the surgery) were anesthetized with 2.5-3.0% halothane (Halocarbon Laboratories), and surgically implanted for sleep recordings. Two screw electrodes were placed in the parietal bone over the hippocampus (P=4.0; L=3.0), to record the electroencephalogram (EEG). Two wire electrodes were placed in the external and internal canthus of the orbit to record eye movements (EOG). Postural tone (EMG) was recorded through two wire electrodes inserted into the neck musculature. A stainless steel cannula (23 gauge) was stereotaxically implanted into the lateral ventricle. Rats were individually housed and the light-dark cycle was controlled (12:12, lights on at 06.30 h)

One week after the surgery, rats were habituated to the recording conditions for at least 2 days. Rats were recorded in a small cage (16×10×10") placed inside of an environmental chamber (35×34×29"). Once the habituation period was completed, rats were divided into five groups (n=5). Each group was challenged with an intraventricular (ICV) administration of a solution of doxylamine succinate or ethanol (EtOH, J. T. Baker). Control animals received 10 #1 of saline. Rats were continuously recorded for 8 h after the ICV injection (1000-1800 h). In addition, rats were observed for changes in spontaneous behavior through a one-way window.

These methods are described in more detail in Prospero-Garcia, O.; Criado J. R. and Henricksen, S. J., A method for investigating sleep Pharmacology of Ethanol and Glutamate Antagonists on Rodent Sleep: A Comparative Study. *Pharmacology Biochemistry and Behavior*, 1994, 49, 413-416.

Acid addition salts of the antihistamine and optional melatonin, 5-hydroxytryptophan and tryptophan combinations and other agents employed in the invention can be prepared in a conventional manner by treating a solution or suspension of the corresponding free base with one chemical equivalent of a pharmaceutically acceptable acid. Conventional concentration or crystallization techniques can be employed to isolate the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related organic or inorganic acids. The antihistamine and optional melatonin, 5-hydroxytryptophan and tryptophan combinations and their pharmaceutically acceptable salts, may be administered alone or in combination with pharmaceutically acceptable carriers, in either single or multiple doses. Suitable pharmaceutical carriers include inert solid diluents or fillers, sterile aqueous solutions, oils (e.g. peanut oil, sesame oil) and various organic solvents. Enterically coated tablets are a preferred formulation when 5-hydroxytryptophan is utilized as one of the indole-based dietary supplements. The pharmaceutical compositions formed by combining the antihistamine and optional melatonin, 5-hydroxytryptophan and tryptophan combinations and pharmaceutically acceptable carriers can be readily administered in a variety of dosage forms such as tablets, powders, lozenges, emulsions, oil soft gels, syrups, injectable solutions and the like. These pharmaceutical compositions can, if desired, contain additional ingredients such as flavorings, binders, excipients, taste-masking agents and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions, elixirs or beverages are desired for oral administration, the essential active ingredient therein may be combined with a large range of various sweetening or flavoring agents, coloring matter or dyes and, if desired, emulsifying or suspending agents, together with diluents such as water, ethanol, propylene glycol, glycerin and combinations thereof.

For parenteral administration, solutions containing the antihistamine and optional melatonin, tryptophan and 5-hydroxy-tryptophan combinations or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

The effective dosages for the antihistamine, melatonin, 5-hydroxytryptophan and tryptophan combinations employed in the methods of this invention will depend on the intended route of administration and factors such as the age and weight of the patient. The dosages will also depend on the particular condition to be treated and will generally range from about 0.1 to about 300 mg/kg body weight of the patient per day, with administration carried out in single or divided dosages.

Although the present invention has been described with reference to specific embodiments, workers skilled in the art will recognize that many variations can be made therefrom. It is to be understood and appreciated that this discovery in accordance with this invention are only those which are illustrated of the many additional potential variations that can be envisioned by one of ordinary skill in the art, and thus are not in any way intended to be limiting of the invention. Accordingly, other objects and advantages of the invention will be apparent to those skilled in the art from the description together with the claims.

The invention claimed is:

1. A pharmaceutical composition for the induction of restorative sleep function comprising an enterically coated tablet, locking capsule or beverage for ingestion and a mixture of an antihistamine drug and two or more indole-based dietary supplements.

2. The composition according to claim 1 wherein the antihistamine drug is selected from a group consisting of Cetirizine, Chlorpheniramine, Clemastine, Desloratadine, Dexchlorpheniramine, Dimenhydrinate, Dimetindene, Diphenhydramine, Doxylamine, Ebastine, Embramine, Fexofenadine, Levocetirizine, Loratadine, Meclozine, Olopatadine, Pheniramine, Promethazine Triprolidine, and pharmaceutically-acceptable salts thereof.

3. The pharmaceutical composition of claim 1 wherein one of the indole-based dietary supplement is L-tryptophan or a derivative of L-tryptophan.

4. The pharmaceutical composition of claim 3 further comprising melatonin and its pharmaceutically acceptable salts.

5. The composition according to claim 1 wherein the antihistamine drug is a metabolite of the compounds selected from a group consisting of Cetirizine, Chlorpheniramine, Clemastine, Dexchlorpheniramine, Dimenhydrinate, Dimetindene, Diphenhydramine, Doxylamine, Ebastine, Embramine, Fexofenadine, Levocetirizine, Loratadine, Meclozine, Olopatadine, Pheniramine, Promethazine Triprolidine, and pharmaceutically-acceptable salts thereof.

6. The composition according to claim 1 further includes at least one vitamin and pharmaceutically acceptable minerals to enhance the effect of the indole-based compounds.

7. The composition according to claim 1 further includes pharmaceutically acceptable calcium salts, magnesium salts, and at least one pyridine-based vitamin.

* * * * *